United States Patent [19]

Liu et al.

[11] Patent Number: 5,079,254

[45] Date of Patent: Jan. 7, 1992

[54] DERIVATIVES OF 6-AMINOOCTAHYDROINDOLIZINETRIOL

[75] Inventors: Paul S. Liu; Mohinder S. Kang, both of Cincinnati, Ohio

[73] Assignee: Merrell Dow Pharmaceuticals Inc., Cincinnati, Ohio

[21] Appl. No.: 532,522

[22] Filed: Jun. 4, 1990

[51] Int. Cl.$^5$ .................. A61K 31/435; C07D 221/00
[52] U.S. Cl. .................................. 514/299; 546/183
[58] Field of Search .................... 546/183; 514/299

[56] References Cited

U.S. PATENT DOCUMENTS 4,871,747 10/1989 Kinast et al. ..................... 514/315

FOREIGN PATENT DOCUMENTS 297534 9/1989 European Pat. Off. ............ 546/183
1129182 6/1986 Japan ................................... 546/183
1277685 12/1986 Japan ................................... 546/183

OTHER PUBLICATIONS

Fleet et al., *Chem. Letters*, 1986, 1051.
Boshagen et al., *Carbohydrate Research*, 164, 141 (1987).
Derwent Patent Abstract 86-247631 (1986)(Abstract of Japanese Kokai 61 129182).

*Primary Examiner*—Cecilia Shen
*Attorney, Agent, or Firm*—John J. Kolano

[57] ABSTRACT

Amide and ester derivatives of 6-amino-octahydro-1,7,8-indolizinetriol are described herein. The compounds are prepared from castanospermine by replacing the appropriate hydroxy function with an amino function while protecting the other hydroxy groups in the meantime. The compounds are useful as hexosaminidase inhibitors.

4 Claims, No Drawings

DERIVATIVES OF 6-AMINOOCTAHYDROINDOLIZINETRIOL

Background of the Invention

A. Chemistry

A number of polyfunctional derivatives of octahydroindolizine have been isolated from natural sources and described in the literature. One such compound which has been investigated extensively is castanospermine, an alkaloid which has been isolated from the seeds of *Castanospermum australe* and which has the following formula:

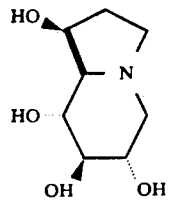

Systematically, this compound can be named in several ways as follows: [1S-(1α,6β,7α,8β,8aβ)]-octahydro-1,6,7,8-indolizinetetrol or (1S,6S,7R,8R,8aR)-1,6,7,8-tetrahydroxyindolizidine or 1,2,4,8-tetradeoxy-1,4,8-nitrilo-L-glycero-D-galacto-octitol. The term "castanospermine" or the first systematic name will be used when referring to compounds having the above basic structure in the discussion below.

B. Utility

Hexosaminidases (β-N-acetyl-glucosaminidase and β-N-acetyl-galactosaminidase) have been found to catalyze the hydrolysis of terminally linked β-N-acetyl-hexosamines of lipid-linked and protein-linked oligosaccharides. Thus, most cell surface glycolipids and glycoproteins are altered during cell growth, differentiation and malignant transformation and this can involve such hexosaminidase catalyzed hydrolyses. Such structural and functional changes in a cell can occur at a multiplicity of sites and can result from changes in tumor cell glycosidase levels. Many of the behavioral changes manifested by tumor cells which ultimately result in uncontrolled cell growth, invasiveness and metastasis have been attributed to cell surface changes in malignancy. Specifically, in connection with oncogenic transformation of cells by chemicals or viruses, an increase in total cellular lysosomal hydrolase activities is often observed.

More specifically, in studies using serum from normal or tumor-bearing rats and mice, hexosaminidase (β-N-acetylglucosaminidase) levels of 5-10 fold higher were observed in the tumor-bearing animals [R. J. Bernacki et al., Cancer and Metastasis Review 4, 81 (1985)]. Similarly, higher levels of β-N-acetyl-glucosaminidase have been found in serum or urine of cancer patients with hepatic, gastrointestinal, human colon, breast carcinoma and gynecological malignancies [H. B. Bosmann et al., Res. Commun. Pathol. Pharmal. 12, 499 (1975); C. H. Lo et al., J. Med. 9, 313 (1978)]. Thus, on this basis, inhibition of hexosaminidases would provide another approach for cancer therapy. In particular, 2-acetamidoglucal, an inhibitor of hexosaminidase has been found to increase by 63% the life span of female mice implanted with Lewis lung tumor cell (Bernacki, page 93).

DESCRIPTION OF THE INVENTION

The present invention is directed to certain substituted derivatives of octahydroindolizine and, more particularly, to 6-amino-substituted derivatives of octahydro-1,7,8-indolizinetriol wherein the substituents are situated at the same positions as the substituents in castanospermine and have the same configuration as the substituents in castanospermine. Specifically the present invention is directed to compounds having the following general formula:

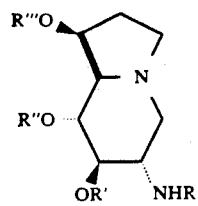

wherein R is $C_{1-10}$ alkanoyl; and R', R" and R'" are independently hydrogen, $C_{1-10}$ alkanoyl or benzoyl.

The $C_{1-10}$ alkanoyl groups referred to above can be straight- or branched-chain and can be exemplified by formyl, acetyl, propionyl, butyryl, isobutyryl, hexanoyl, octanoyl and decanoyl.

Acid addition salts of the above compounds with pharmaceutically acceptable acids are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Preferred compounds of the present invention are those wherein R', R" and R'" are hydrogen.

Some examples of specific compounds within the scope of the present invention and useful therein are the following:

[1S-(1α,6β,7α,8β,8aβ)]-6-Acetamidooctahydro-1,7,8-indolizinetriol 7-acetate

[1S-(1α,6β,7α,8β,8aβ)]-6-Acetamidooctahydro-1,7,8-indolizinetriol 7-butyrate

[1S-(1α,6β,7α,8β,8aβ)]-6-Acetamidooctahydro-1,7,8-indolizinetriol 7-benzoate

[1S-(1α,6β,7α,8β,8aβ)]-6-Acetamidooctahydro-1,7,8-indolizinetriol 1,8-diacetate

[1S-(1α,6β,7α,8β,8aβ)]-6-Acetamidooctahydro-1,7,8-indolizinetriol 1,8-dibenzoate

[1S-(1α,6β,7α,8β,8aβ)]-6-Acetamidooctahydro-1,7,8-indolizinetriol 1,7,8-triacetate

[1S-(1α,6β,7α,8β,8aβ)]-6-Acetamidooctahydro-1,7,8-indolizinetriol 7-benzoate 1,8-diacetate

[1S-(1α,6β,7α,8β,8aβ)]-6-Butyramidooctahydro-1,7,8-indolizinetriol

The amides of the present invention are prepared by the reaction of a 6-aminooctahydroindolizine of the formula

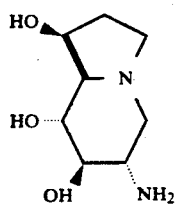

with an acid halide of the formula R—X or an acid anhydride of the formula R₂O, wherein R is defined as above and X is chlorine or bromine, in the presence of water, to give the corresponding amide. This amide can then be reacted further with the same acid halide or acid anhydride, under anhydrous conditions to give a mixture of esters which are separated by chromatography. Control of the amount of acid halide or anhydride determines the extent of esterification which takes place with larger amounts giving more esterification. Alternatively, such esters can also be obtained by a series of standard protection and deprotection reactions similar to those described below for the preparation of the amino starting material used above.

The amine starting material shown above is generally not used in isolated form but is prepared in situ by catalytic hydrogenation of the corresponding azide using palladium on carbon as the catalyst and the solution of the amine that results is used as described. In that situation the azide in which the hydroxy groups are esterified can be used to give the corresponding ester product although, in the case of any 7-ester, the acyl group will migrate to the nitrogen when the amine is formed to give the corresponding amide which has a free 7-hydroxy group.

The amine/azide starting material referred to above can be obtained from castanospermine in a series of reactions in which the 1-, 7- and 8-hydroxy groups are protected in various appropriate ways while the 6-hydroxy function is transformed as desired. Thus, for example, castanospermine is reacted with benzoyl chloride in pyridine to give castanospermine 6,7-dibenzoate. This dibenzoate is then reacted with 2-methoxypropene or 1-methoxycyclohexene and acid to introduce the 1,8-O-isopropylidene or 1,8-O-cyclohexylidene group and the two benzoate ester groups are removed by hydrolysis with base such as sodium hydroxide or by transesterification with sodium or potassium alkoxide as the catalyst. The resulting 6,7-dihydroxy compound is reacted with benzyloxycarbonyl chloride in the presence of a tertiary amine such as triethyl amine to give the corresponding 6-O-benzyloxycarbonyl compound, which still contains a free 7-hydroxy group.

The resulting 7-hydroxy compound is then reacted with an aromatic acid chloride in the presence of a tertiary amine to give the corresponding 7-ester. 4-Bromobenzoyl chloride is advantageous in this reaction because it is more reactive than acid chlorides such as benzoyl chloride, but benzoyl chloride or similar acid halides can still be used.

The ketal group can then be removed by treating the compound with methanolic hydrogen chloride and the resulting 1,8-dihydroxy compound is reacted with acetic anhydride in pyridine to give the corresponding 1,8-diacetate. Alternatively, the ketal group can be removed after the 6-O-benzyloxycarbonyl ester is formed and the resulting 1,7,8-trihydroxy compound is reacted with excess acetic anhydride in pyridine to give the 1,7,8-triacetate. In either case, the benzylcarbonate with no free hydroxy groups is then hydrogenated using palladium on charcoal catalyst in the presence of cyclohexene. This give the corresponding free 6-hydroxy compound and, if a 4-bromobenzoate is used, the bromine is removed at the same time by hydrogenolysis. The 6-hydroxy group is then reacted with methanesulfonyl chloride to give the corresponding 6-methanesulfonate. This 6-sulfonate is then reacted with sodium iodide in 2-butanone to give the corresponding 6-iodide, which has the opposite configuration, and that iodide is further reacted with sodium azide to give the desired 6-azide in which the configuration of the azide is the same as the original 6-hydroxy group in castanospermine. The azide is then treated with a strong base, such as sodium methoxide in methanol, to remove the ester groups at the other three positions.

The compounds according to this invention are useful as a result of their pharmacological activity. Thus, they inhibit extra- and intra-cellular carbohydrate metabolism, glycosyl transferase, and also glucosidase. In addition, they affect glycoprotein- and chitin-biosynthesis and act as fungicides, bacteriostats, immunomodulators and insecticides. The present compounds can further be described as hexosaminidase inhibitors.

On the basis of the above properties, the present compounds can be used in treating the following disorders: prediabetes, gastritis, obstipation, caries, atherosclerosis, diabetes, hyperlipoproteinemia or tumors controlled by hexosaminidase.

Inhibition of hexosaminidase activity by the compounds of the present invention can be demonstrated by the following test procedure using 4-nitrophenyl-N-acetyl-β-glucosaminide substrate in a reaction mixture with a final total volume of 200 μl and using a 96-well microplate. In a preliminary screen, test compounds are studied over a range of concentrations from 0.1 to 100 μg/ml. together with a control sample. Specifically, the test compound is added to individual wells and made up to a total volume of 100 μl. To each well is added 25 μl of 1M sodium citrate buffer pH 4.5 and 25 μl of enzyme (1 mμ) in 10 mM sodium citrate at pH 4.5. The material is mixed and incubated at room temperature for 10 minutes. Then 50 μl of 10 mM substrate (4-nitrophenyl-N-acetyl-8-glucosaminide, Sigma # N-91376) is added and the mixture is incubated at 37° C. for 30 minutes. The reaction is then killed by adding 100 μl of 2% sodium carbonate and the yellow color due to release of 4-nitrophenol is read at 405 nm in an Elisa reader. The results obtained in this preliminary screen are then examined and, if inhibition has taken place, the procedure is repeated using several concentrations over a narrower range to provide for a more precise determination of the IC₅₀. When [1S-(1α,6β,7α,8β,8aβ)]-6-acetamidooctahydro-1,7,8-indolizinetriol was tested in this way, it showed an IC₅₀ value of 0.1 μg/ml for the inhibition of hexosaminidase from human placenta and porcine placenta.

The present invention also relates to a method of inhibiting hexosaminidase activity in mammals, including humans, which comprises administering internally to a subject in need of such inhibition an effective amount of an octahydroindolizine of the present invention. Although careful consideration should be given to the dosage and the dosage regimen in each individual case, by taking into account the age, the weight and the condition of the subject and the nature and severity of the disease involved and by the use of well-founded expert judgment, the dosage will usually be in the range of about 1 to about $1 \times 10^4$ SIU/kg of body weight per day. In some cases, an adequate therapeutic effect will be achieved with a lower dose than this, whereas in other cases a larger dose will be necessary.

In using the compounds of this invention for the purposes described above, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions, wettable and effervescent powders and solutions suitable for injection intravenously and intraperitoneally, and can contain suitable excipients known to be useful in the preparation of the particular type of composition desired. Suitable pharmaceutical carriers and formulation techniques are found in standard texts, such as *Remington's Pharmaceutical Sciences*, Mack Publishing Company, Easton, Pa.

The following examples are presented to illustrate this invention but they should not be construed as limiting it in any way.

EXAMPLE 1A

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0°-4° C. for 7 days. Water, 10 ml, was added and the mixture was evaporated to dryness in vacuo. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf=0.42 and Rf=0.11). The mixture was separated by preparative high pressure liquid chromatography (silica gel, 1:1 ethyl acetate:hexane) to provide 1.9 g (48%) of the more polar [1S-(1α,6β,7α,8α,8aβ)]-octahydro-1,6,7,8-indolizinetetrol 6,7-dibenzoate as a dry foam melting at about 79°-81° C. NMR (DMSO-d$_6$/D$_2$O) ⊕ 1.5-2.3 (m, 5H), 3.0-3.4 (m, 2H), 3.9 (t, 1H), 4.2 (m, 1H, C$_1$-H), 5.15 (m, 1H, C$_6$-H), 5.3 (t, 1H, C$_7$-H), 7.4-8.0 (m, 10H, aryl). MS (FAB-Xe) 398 (MH+), 380 (MH+-H$_2$O), 276 (MH+-PhCO$_2$H). The less polar component (Rf=0.42) was isolated as a dry foam melting at about 75°-78° C. which was [1S-(1α,6β,7α,8β,8aβ)]-octahydro-1,6,7,8-indolizinetetrol 6,7-tribenzoate.

EXAMPLE 1B

Castanospermine (38 g) was added to 250 ml of pyridine and the mixture was cooled at 0° C. while 27.9 g of benzoyl chloride was added dropwise. After this addition was complete, the mixture was stirred at room temperature for 4 hours and then cooled again to 0° C. An additional 27.9 g of benzoyl chloride was added and the mixture was stirred at room temperature for 6 days. After dilution with 20 ml of water, the mixture was evaporated to dryness in vacuo to leave a syrupy golden residue which was stirred vigorously with 100 ml of 3 N hydrochloric acid and 400 ml of methylene chloride. The white amorphous solid which formed was [1S-(1α,6β,7α,8β,8aβ)]-octahydro-1,6,7,8-indolizinetetrol 6,7-dibenzoate hydrochloride and this was separated by filtration and dried to give a solid melting at 229°-231° C.

EXAMPLE 2

A mixture of 5.0 g of [1S-(1α,6β,7α,8β,8aβ)]-octahydro-1,6,7,8-indolizinetetrol 6,7-dibenzoate hydrochloride, 100 ml of 1,2-dimethoxyethane, 22 ml of 2-methoxypropene and 0.22 g of 4-toluenesulfonic acid monohydrate was refluxed with stirring for 1.5 hours to give a clear solution. The reaction was cooled to 25° C. and diluted with 30 ml of saturated aqueous sodium bicarbonate solution and 60 ml of water. This solution was then extracted twice with methylene chloride and the combined organic extracts were dried over magnesium sulfate and the solvent was evaporated in vacuo to give a light green foam. This material was recrystallized from pentane to give [1S-(1α,6β,7α,8β,8aβ)]-1,8-O-isopropylideneoctahydro-1,6,7,8-indolizinetetrol 6,7-dibenzoate as white crystals melting at about 132°-133° C. (78.6% yield).

[1S-(1α,6β,7α,8β,8aβ)]-1,8-O-isopropylideneoctahydro-1,6,7,8-indolizinetetrol 6,7-dibenzoate (11.07 g, 25.3 mmol) was added to methanol (150 mL) and stirred at room temperature. To the above slurry was added 25 drops of sodium methoxide (25% solution in methanol) and the mixture was stirred under nitrogen atmosphere for 20 hours. The methanolic solution was evaporated to a gummy syrup which was flash chromatographed (silica gel, eluent: 8/2 ethyl acetate/methanol) to provide [1S-(1α,6β,7α,8β,8aβ)]-1,8-O-isopropylideneoctahydro-1,6,7,8-indolizinetetrol as a dry foamy solid (5.23 g, 90%). $^1$H NMR (CDCl$_3$) δ 1.39 (s, 3H), 1.41 (s, 3H), 1.9 (m, 1H), 2.25 (m, 1H), 2.8 (m, 2H), 3.0 (m, 2H), 3.25 (dd, 1H), 3.5 (dd, 1H), 3.65 (t, 1H), 3.8 (m, 1H), 4.5 (t, 1H). MS (CI-CH$_4$) 230 (MH+).

EXAMPLE 3

To a solution of [1S-(1α,6β,7α,8β,8aβ)]-1,8-O-isopropylideneoctahydro-1,6,7,8-indolizinetetrol (11.0 g, 48 mmol) in methylene chloride (300 mL) containing triethylamine (10.2 g, 100 mmol) and N,N-dimethylaminopyridine (0.3 g), was added dropwise benzyl chloroformate (17 g, 100 mmol). After stirring for 1 h, water (50 mL) was added and the phases were separated. The organic layer was washed with saturated aqueous sodium bicarbonate solution (300 mL), dried over magnesium sulfate and evaporated to provide a syrupy residue. The residue was purified by flash chromatography (1:1 ethyl acetate:hexane) to provide as the less polar component, the oily 1,8-O-isopropylidene-6,7-di-O-carbobenzyloxy-castanospermine (3.8 g, 16%). The more polar component, [1S-(1α,6β,7α,8β,8aβ)]-1,8-O-isopropylideneoctahydro-1,6,7,8-indolizinetetrol 6-benzylcarbonate (12.2 g, 70%) was isolated as a thick oil. $^1$H NMR (CDCl$_3$) δ 1.4 (2s, 2×3H), 1.9 (m, 1H), 2.2 (m, 1H), 2.8-2.9 (m, 2H), 3.0 (m, 2H), 3.4 (dd, 1H), 3.7 (m, 2H), 4.5 (m, 1H), 4.8 (m, 1H), 5.2 (s, 2H), 7.3-7.4 (m, 5H). MS (CI—CH$_4$) 364 (MH+), 346 (MH+—H$_2$O).

EXAMPLE 4

To a solution of [1S-(1α,6β,7α,8β,8aβ)]-1,8-O-isopropylideneoctahydro-1,6,7,8-indolizinetetrol 6-benzylcarbonate (1.45 g, 4 mmol) in methylene chloride (50 mL) was added triethylamine (0.6 g, 6 mmol), N,N-dimethylaminopyridine (100 mg) and 4-bromobenzoyl chloride (1.27 g, 5.8 mmol) and the mixture was stirred at room temperature for 18 h. After addition of water (20 mL), the phases were mixed thoroughly and separated. The organic layer was washed with brine (20 mL) and saturated sodium bicarbonate solution (20 mL) and finally dried ($MgSO_4$). Evaporation of solvent from the organic phase gave a syrupy residue which was dissolved in ether (40 mL). Upon cooling and slow evaporation, [1S-(1α,6β,7α,8β,8aβ)]-1,8-O-isopropylideneoctahydro-1,6,7,8-indolizinetetrol 6-benzylcarbonate 7-(4-bromobenzoate) crystallized as colorless needles and was collected (1.83 g, 84%). m.p. 139°–141° C. IR (KBr) 1744 $cm^{-1}$ (C=O); $^1$H NMR ($CDCl_3$) δ 1.25 (s, 3H), 1.35 (s, 3H), 1.8–2.3 (m, 2H), 2.8–3.4 (m, 5H), 3.9 (t, 1H), 4.55 (m, 1H), 5.05 (s, 2H), 5.1 (m, 1H, $H_6$), 5.3 (t, 1H, $H_7$), 7.1–7.4 (m, 5H), 7.55 (d, 2H), 7.9 (d, 2H). MS (CI—$CH_4$) 546 (MH+), 488 (MH+—$CH_3COCH_3$).

EXAMPLE 5

To a stirred suspension of [1S-(1α,6β,7α,8β,8aβ)]-1,8-O-isopropylideneoctahydro-1,6,7,8-indolizinetetrol 6-benzylcarbonate 7-(4-bromobenzoate) (2.2 g, 4.03 mmol) in methanol (20 mL) was added a saturated solution of dry hydrogen chloride in methanol (10 mL) and the mixture was kept at room temperature for 2 hours. The solvent was evaporated by a stream of dry nitrogen and the resulting residue was dissolved in a mixture of ethyl acetate (10 mL) and methylene chloride (50 mL). The organic solution was washed twice with saturated sodium bicarbonate solution (20 mL). The organic phase was dried ($MgSO_4$) and slowly evaporated upon which [1S-(1α,6β,7α,8β,8aβ)]-octahydro-1,6,7,8-indolizinetetrol 6-benzylcarbonate 7-(4-bromobenzoate) crystallized as a colorless solid (1.84 g, 90%). m.p. 181°–4° C. IR (KBr) 1744, 1716 $cm^{-1}$ (C=O); 1H NMR ($CDCl_3$) δ 1.8–2.4 (m, 5H), 3.2 (m, 1H), 3.4 (dd, 1H), 4.0 (m, 1H), 4.45 (m, 1H), 5.05 (s, 2H), 5.1–5.2 (m, 2H), 7.1–7.9 (m, 9H, aryl). MS (CI—$CH_4$) 506 (MH+), 488 (MH+—$H_2O$), 354 (MH+—$PhCH_2$—O—COOH).

EXAMPLE 6

To a solution of [1S-(1α,6β,7α,8β,8aβ)]-octahydro-1,6,7,8-indolizinetetrol 6-benzylcarbonate 7-(4-bromobenzoate) (510 mg, 1 mmol) in pyridine (5 mL) was added dropwise a solution of acetic anhydride (1 mL, 10.6 mmol) and the mixture was kept under stirring for 3 days at room temperature. The resulting mixture was evaporated to dryness in vacuo and the residue was redissolved in ethyl acetate (100 mL). The organic solution was washed with brine (50 mL) and saturated sodium bicarbonate solution (50 mL) and finally dried ($MgSO_4$). Evaporation of solvent from the above extract provided a yellowish oil, [1S-(1α,6β,7α,8β,8aβ)]-octahydro-1,6,7,8-indolizinetetrol 1,8-diacetate 6-benzylcarbonate 7-(4-bromobenzoate) (500 mg, 85%), pure by TLC ($R_f$=0.33, silica gel TLC, 1:2 ethyl acetate:hexane). IR (KBr) 1754 $cm^{-1}$ (C=O); 1H NMR ($CDCl_3$) δ 1.85 (s, 3H), 1.90 (m, 1H), 2.05 (s, 3H), 2.2–2.5 (m, 4H), 3.25 (dd, 1H), 3.5 dd, 1H), 5.05 (s, 2H), 5.1 (m, 1H), 5.25–5.50 (m, 3H), 7.1–7.3 (m, 5H), 7.5–7.6 (d, 2H), 7.8 (d, 2H). MS (CI—$CH_4$) 590 (MH+), 530 (MH+—$CH_3CO_2H$).

EXAMPLE 7

To a solution of [1S-(1α,6β,7α,8β,8aβ)]-octahydro-1,6,7,8-indolizinetetrol 1,8-diacetate 6-benzylcarbonate 7-(4-bromobenzoate) (2.8 g, 4.75 mmol) in methanol (25 mL) containing cyclohexene (25 mL) was added a mixture of 10% Pd/C (300 mg) and ethanol (2 mL). The resulting mixture was stirred and heated under reflux for 6 hours. After cooling, the solution was filtered through Celite and the filtrate was evaporated to dryness. The resultant residue was dissolved in ethyl acetate (200 mL) and washed twice with saturated sodium bicarbonate solution (50 mL). The organic phase was dried ($MgSO_4$) and evaporated in vacuo to provide [1S-(1α,6β,7α,8β,8aβ)]-octahydro-1,6,7,8-indolizinetetrol 1,8-diacetate 7-benzoate as an oil (1.62 g, 91%). IR (KBr) 1738 $cm^{-1}$ (C=O); $^1$H NMR ($CDCl_3$) δ 1.8 (s, 3H), 2.0 (s, 3H), 1.7–2.5 (m, 5H), 3.0–3.4 (m, 2H), 3.9 (m, 1H), 4.8–5.4 (m, 3H), 7.3–7.6 (m, 3H), 7.9–8.1 (m, 2H); MS (CI—$CH_4$) 378 (MH+), 360 (MH+—$H_2O$), 318 (MH+—$CH_3CO_2H$).

EXAMPLE 8

To a solution of [1S-(1α,6β,7α,8β,8aβ)]-octahydro-1,6,7,8-indolizinetetrol 1,8-diacetate 7-benzoate (0.80 g, 2.1 mmol) in a (2:1) mixture of methylene chloride and tetrahydrofuran (30 mL) containing triethylamine (1.0 mL) was added dropwise a solution of methanesulfonyl chloride (0.5 mL, 6.5 mmol). After stirring for 30 min, the reaction mixture was diluted with methylene chloride (30 mL) and washed with brine (100 mL), saturated sodium bicarbonate solution (100 mL) and brine (100 mL) again. The organic phase was dried ($MgSO_4$) and evaporated in vacuo to provide the 6-methanesulfonate as an oil. The crude product was redissolved in 2-butanone (25 mL) and sodium iodide (1.0 g, 6.67 mmol) was added and the mixture was heated under reflux with stirring for 4 hours upon which all of the methanesulfonate was converted to a less polar material (1:2 ethyl acetate: hexane, silica gel TLC). The mixture was cooled and evaporated to dryness. The residue was dissolved in ethyl acetate (100 mL) containing brine (20 mL). The organic phase was washed successively with 10% sodium bisulfite solution (50 mL), saturated sodium bicarbonate solution (50 mL) and brine (50 mL). After drying ($MgSO_4$), the organic solution was evaporated to provide the 6-deoxy-6-iodo-compound as an oil (0.79 g, 86%). The crude iodo-derivative was dissolved in dimethylformamide (10 mL) containing sodium azide (0.2 g). The mixture was stirred and heated at 85°–90° C. for 6 hours. The mixture was cooled, diluted with ethyl acetate (100 mL) and washed with 50% saturated brine (2×100 mL). The organic phase was concentrated and purified by flash chromatography to provide the 68-azido-6-deoxy-derivative, [1S-(1α,6β,7α,8β,8aβ)]-6-azidooctahydro-1,7,8-indolizinetriol 1,8-diacetate 7-benzoate, as an oil (0.49 g, 75%). IR (KBr) 2106 $cm^{-1}$ (—$N_3$), 1740 $cm^{-1}$(C=O); $^1$H NMR ($CDCl_3$) δ 1.8 (s, 3H), 2.0 (s, 3H), 1.9–2.4 (m, 5H), 3.0–3.9 (m, 3H), 5.1–5.7 (m, 3H), 7.2–7.6 (m, 3H), 7.8–8.1 (m, 2H). MS (CI—$CH_4$) 403 (MH+), 360 (MH+—$HN_3$), 343 (MH+—$CH_3CO_2H$).

EXAMPLE 9

To a solution of [1S-(1α,6β,7α,8β,8aβ)]-6-azidooctahydro-1,7,8-indolizinetriol 1,8-diacetate 7-benzoate (0.49 g) in methanol was added 2 drops of 25% sodium methoxide solution in methanol and the mixture was stirred at room temperature for 18 hours. The reaction mixture was evaporated to dryness and redissolved in water (10 mL). The aqueous solution was washed twice with ethyl acetate (20 mL each) and mixed with 10% Pd/C (100 mg). The mixture was hydrogenated at 2.7 atmospheres for 18 hours and filtered. The clear aqueous filtrate, which contains [1S-(1α,6β,7α,8β,8aβ)]-6-aminooctahydro-1,7,8-indolizinetriol, was diluted with acetone (10 mL) and acetic anhydride (5 drops) was added. After stirring for 2 days at room temperature, the mixture was evaporated to dryness in vacuo and the residue was redissolved in methanol and flash chromatographed (silica gel, eluent: (3/7) methanol/ethyl acetate) to provide [1S-(1α,6β,7α,8β,8aβ)]-6-acetamidooctahydro-1,7,8-indolizinetriol as a colorless solid (215 mg, 83%). m.p. 199°–203° C. (with decomp.). IR (KBr) 3600–3100 cm$^{-1}$ (br, —OH), 1636 cm$^{-1}$ (—C=O); $^1$H NMR (D$_2$O) δ 1.6–1.8 (m, 1H), 1.9–2.1 (m, 5H), 2.15–2.4 (m, 2H), 3.0–3.15 (m, 2H), 3.4 (t, J $_{6,7}$=10 Hz, 1H, H$_7$), 3.65 (t, J $_{7,8}$=9 Hz, 1H, H$_8$), 3.85 (m, 1H, H$_6$), 4.4 (m, 1H, H$_1$). MS (CI—CH$_4$) 231 (MH$^+$), 213 (MH$^+$—H$_2$O). This compound has the following structural formula:

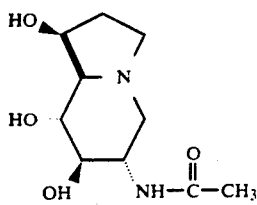

What is claimed is:

1. A compound of the formula

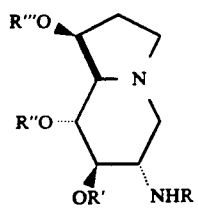

wherein R is C$_{1-10}$ alkanoyl; and R', R" and R''' are independently hydrogen, C$_{1-10}$ alkanoyl or benzoyl.

2. A compound according to claim 1 which is [1S-(1α,6β,7α,8β,8aβ)]-6-acetamidooctahydro-1,7,8-indolizinetriol.

3. A method of inhibiting hexosaminidase activity in mammals which comprises administering internally to a subject in need of such inhibition an effective amount of a compound of the formula

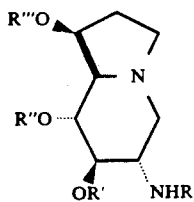

wherein R is C$_{1-10}$ alkanoyl; and R', R" and R''' are independently hydrogen, C$_{1-10}$ alkanoyl or benzoyl.

4. A method according to claim 3 wherein the compound is [1S-(1α,6β,7α,8β,8aβ)]-6-acetamidooctahydro-1,7,8-indolizinetriol.

* * * * *